(12) United States Patent
Cassayre et al.

(10) Patent No.: US 9,339,505 B2
(45) Date of Patent: *May 17, 2016

(54) PESTICIDAL MIXTURES INCLUDING ISOXAZOLINE DERIVATIVES

(75) Inventors: Jerome Yves Cassayre, Stein (CH); Myriem El Qacemi, Stein (CH)

(73) Assignee: Syngenta Participations AG, Basel (CH)

( * ) Notice: Subject to any disclaimer, the term of this patent is extended or adjusted under 35 U.S.C. 154(b) by 13 days.

This patent is subject to a terminal disclaimer.

(21) Appl. No.: 14/119,912

(22) PCT Filed: May 30, 2012

(86) PCT No.: PCT/EP2012/060107
§ 371 (c)(1),
(2), (4) Date: Nov. 25, 2013

(87) PCT Pub. No.: WO2012/163948
PCT Pub. Date: Dec. 6, 2012

(65) Prior Publication Data
US 2014/0107057 A1    Apr. 17, 2014

(30) Foreign Application Priority Data
May 31, 2011    (EP) .................................... 11168223

(51) Int. Cl.
*A61K 31/5377* (2006.01)
*A01N 43/80* (2006.01)
*A61K 31/422* (2006.01)
*A61K 31/427* (2006.01)
*A61K 31/433* (2006.01)
*A61K 31/4439* (2006.01)
*A61K 31/4709* (2006.01)
*A61K 45/06* (2006.01)

(52) U.S. Cl.
CPC ............ *A61K 31/5377* (2013.01); *A01N 43/80* (2013.01); *A61K 31/422* (2013.01); *A61K 31/427* (2013.01); *A61K 31/433* (2013.01); *A61K 31/4439* (2013.01); *A61K 31/4709* (2013.01); *A61K 45/06* (2013.01)

(58) Field of Classification Search
CPC .................................................... A61K 31/5377
See application file for complete search history.

(56) References Cited

U.S. PATENT DOCUMENTS 8,735,362 B2 * 5/2014 Cassayre et al. ................ 514/30

FOREIGN PATENT DOCUMENTS

| WO | 2010086225 | 8/2010 |
|----|------------|--------|
| WO | 2010108733 | 9/2010 |
| WO | 2011067272 | 6/2011 |

OTHER PUBLICATIONS

International Search Report and Written Opinion for International Patent Application No. PCT/EP2012/060107 dated Jul. 24, 2012.

* cited by examiner

*Primary Examiner* — Paul Zarek
(74) *Attorney, Agent, or Firm* — Brian D. McAlhaney

(57) ABSTRACT

The present invention provides a combination product comprising a component A and a component B, wherein component A is a compound of formula (I) wherein $A^1$, $A^2$, L, p, $R^1$, $R^2$, $R^3$, $R^4$ and $R^5$ are as defined in claim 1 and component B is a further therapeutic agent; wherein the combination product is for use in a method of therapeutic treatment.

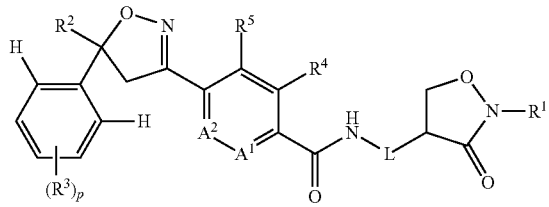

(I)

11 Claims, No Drawings

PESTICIDAL MIXTURES INCLUDING ISOXAZOLINE DERIVATIVES

RELATED APPLICATION INFORMATION

This application is a 371 of PCT Application No. PCT/EP2012/060107, filed 30 May 2012, which claims the benefit of European Patent Application No. 11168223.3 filed 31 May 2011, the contents of which are incorporated herein by reference.

The present invention relates to mixtures of pesticidally active ingredients and to methods of using the mixtures in the field of animal health.

EP1731512 discloses that certain isoxazoline compounds have insecticidal activity.

The present invention provides a combination product comprising a component A and a component B, wherein component A is a compound of formula (I)

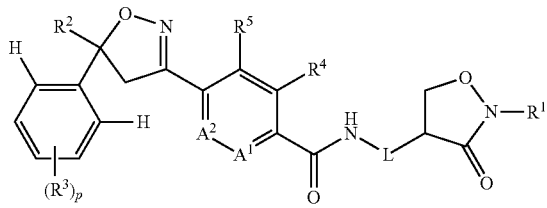

(I)

wherein

L is a direct bond or methylene;

$A^1$ and $A^2$ are C—H, or one of $A^1$ and $A^2$ is C—H and the other is N;

$R^1$ is hydrogen, cyano, cyano-$C_1$-$C_8$alkyl, $C_1$-$C_8$alkyl, $C_1$-$C_8$haloalkyl, $C_3$-$C_8$cycloalkyl, $C_3$-$C_8$cycloalkyl where one carbon atom is replaced by O, S, S(O) or $SO_2$, or $C_3$-$C_8$cycloalkyl-$C_1$-$C_8$alkyl, $C_3$-$C_8$cycloalkyl-$C_1$-$C_8$alkyl where one carbon atom in the cycloalkyl group is replaced by O, S, S(O) or $SO_2$, or $C_3$-$C_8$cycloalkyl-$C_1$-$C_8$haloalkyl, $C_1$-$C_8$hydroxyalkyl, $C_1$-$C_8$alkoxy-$C_1$-$C_8$alkyl, $C_2$-$C_8$alkenyl, $C_2$-$C_8$haloalkenyl, $C_2$-$C_8$alkynyl, $C_2$-$C_8$haloalkynyl, phenyl, phenyl substituted by one to three $R^6$, phenyl-$C_1$-$C_4$alkyl, phenyl-$C_1$-$C_4$alkyl wherein the phenyl moiety is substituted by one to three $R^6$, 5-6 membered heteroaryl-$C_1$-$C_4$alkyl or 5-6 membered heteroaryl-$C_1$-$C_4$alkyl wherein the heteroaryl moiety is substituted by one to three $R^6$, or $C_1$-$C_4$alkyl-($C_1$-$C_4$alkyl-O—N=)C—$CH_2$—;

$R^2$ is chlorodifluoromethyl or trifluoromethyl;

each $R^3$ is independently bromo, chloro, fluoro or trifluoromethyl;

$R^4$ is hydrogen, halogen, methyl, halomethyl or cyano;

$R^5$ is hydrogen;

or $R^4$ and $R^5$ together form a bridging 1,3-butadiene group;

each $R^6$ is independently halogen, cyano, nitro, $C_1$-$C_8$alkyl, $C_1$-$C_8$haloalkyl, $C_1$-$C_8$alkoxy, or $C_1$-$C_8$haloalkoxy;

p is 2 or 3;

and component B is a further therapeutic agent;

wherein the combination product is for use in a method of therapeutic treatment.

The compounds of formula I have outstanding insecticidal properties as described in PCT/EP2010/068605. The components B are known, e.g. from "The Pesticide Manual", Fifteenth Edition, Edited by Clive Tomlin, British Crop Protection Council. Reference to the above components B includes reference to their salts and any usual derivatives, such as ester derivatives.

Preferred substituents are, in any combination, as set out below.

$A^1$ and $A^2$ are preferably C—H.

$R^1$ is preferably hydrogen, cyano-$C_1$-$C_8$alkyl, $C_1$-$C_8$alkyl, $C_3$-$C_8$cycloalkyl, $C_3$-$C_8$cycloalkyl where one carbon atom in the cycloalkyl group is replaced by O, S, S(O) or $SO_2$, or $C_3$-$C_8$cycloalkyl-$C_1$-$C_8$alkyl, $C_3$-$C_8$cycloalkyl-$C_1$-$C_8$alkyl where one carbon atom in the cycloalkyl group is replaced by O, S, S(O) or $SO_2$, or $C_1$-$C_8$haloalkyl, $C_1$-$C_8$hydroxyalkyl, $C_1$-$C_8$hydroxyalkyl, $C_2$-$C_8$alkenyl, $C_2$-$C_8$alkynyl, phenyl-$C_1$-$C_4$alkyl or phenyl-$C_1$-$C_4$alkyl wherein the phenyl moiety is substituted by one to three $R^6$, 5-6 membered heteroaryl-$C_1$-$C_4$alkyl or 5-6 membered heteroaryl-$C_1$-$C_4$alkyl wherein the heteroaryl moiety is substituted by one to three $R^6$; more preferably $R^1$ is hydrogen, cyano-$C_1$-$C_8$alkyl-, $C_1$-$C_8$alkyl, $C_3$-$C_8$cycloalkyl, $C_3$-$C_8$cycloalkyl where one carbon atom in the cycloalkyl group is replaced by O, S, S(O) or $SO_2$, or $C_1$-$C_8$haloalkyl, $C_1$-$C_8$hydroxyalkyl, $C_2$-$C_8$alkenyl, $C_2$-$C_8$alkynyl, phenyl-$C_1$-$C_4$alkyl or phenyl-$C_1$-$C_4$alkyl wherein the phenyl moiety is substituted by one to three $R^6$, 5-6 membered heteroaryl-$C_1$-$C_4$alkyl or 5-6 membered heteroaryl-$C_1$-$C_4$alkyl wherein the heteroaryl moiety is substituted by one to three $R^6$; even more preferably $R^1$ is hydrogen, cyano-$C_1$-$C_6$alkyl, $C_1$-$C_6$alkyl, $C_3$-$C_6$cycloalkyl, $C_3$-$C_6$cycloalkyl where one carbon atom in the cycloalkyl group is replaced by O, S, S(O) or $SO_2$, or $C_1$-$C_6$haloalkyl, $C_1$-$C_6$hydroxyalkyl, $C_1$-$C_6$alkoxy-$C_1$-$C_6$alkyl, $C_2$-$C_6$alkenyl, $C_2$-$C_6$alkynyl, phenyl-$CH_2$-alkyl or phenyl-$CH_2$— wherein the phenyl moiety is substituted by one to three $R^6$, furanyl or furanyl substituted by one to three $R^6$, triazolyl or triazolyl optionally substituted by one to three $R^6$; yet even more preferably $R^1$ is hydrogen, $C_1$-$C_4$alkyl, $C_3$-$C_6$cycloalkyl, $C_1$-$C_4$haloalkyl, $C_1$-$C_4$hydroxyalkyl, $C_1$-$C_4$alkoxy-$C_1$-$C_4$alkyl, phenyl-$CH_2$-alkyl- or phenyl-$CH_2$— wherein the phenyl moiety is substituted by one to three $R^6$, furanyl or furanyl substituted by one to three $R^6$, thietanyl, oxetanyl, oxo-thietanyl, or dioxo-thietanyl; yet even more preferably $R^1$ is hydrogen, methyl, ethyl, propyl, butyl, cyclopropyl, cyclopropyl-methyl, cyclobutyl, cyclobutyl-methyl, oxetanyl, thietanyl, trifluoroethyl, difluoroethyl, allyl, propargyl, cyanomethyl, cyanoethyl, benzyl, benzyl substituted by one to three $R^6$, or $R^1$ is pyridyl-methyl- or pyridyl-methyl-substituted by one to three $R^6$; yet even more preferably $R^1$ is methyl, ethyl, cyclopropyl, cyclobutyl, oxetanyl, thietanyl, trifluoroethyl, difluoroethyl, allyl, propargyl, cyanomethyl, cyanoethyl, benzyl, benzyl substituted by one to three $R^6$, or pyridine-methyl- or pyridine-methyl-substituted by one to three $R^6$, even more preferably methyl, ethyl, cyclopropyl, cyclobutyl, oxetanyl, thietanyl, trifluoroethyl, difluoroethyl, allyl, propargyl, cyanomethyl, cyanoethyl, benzyl, or pyridine-methyl-. Ethyl and trifluoroethyl are particularly preferred. Heteroaryl preferably refers to pyridyl, pyridazinyl, pyrimidinyl, pyrazinyl, pyrazolyl, furanyl, thiophenyl, oxazolyl, isoxazolyl or thiazolyl, more preferably pyridyl, pyrazolyl, furanyl, thiophenyl or thiazolyl, most preferably pyridyl.

$R^2$ is preferably trifluoromethyl.

each $R^3$ is preferably chlorine.

$R^4$ is preferably chloro or methyl, more preferably methyl.

$R^5$ is preferably hydrogen.

Each $R^6$ is preferably independently halogen, cyano, $C_1$-$C_8$haloalkyl, $C_1$-$C_8$alkoxy or $C_1$-$C_8$haloalkoxy, most preferably fluoro, chloro, bromo, trifluoromethyl, trifluoromethoxy, cyano or methoxy.

p is preferably 2.

In one embodiment $A^1$ and $A^2$ are C—H; $R^2$ is trifluoromethyl, and $R^5$ is hydrogen.

In one embodiment $A^1$ and $A^2$ are C—H; $R^2$ is trifluoromethyl, $R^4$ is methyl, $R^5$ is hydrogen, each $R^3$ is chlorine, p is 2.

Compounds of formula I include at least one chiral centre and may exist as compounds of formula I* or compounds of formula I**.

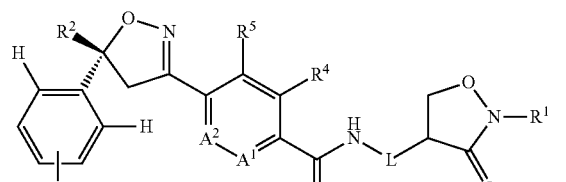

(I*)

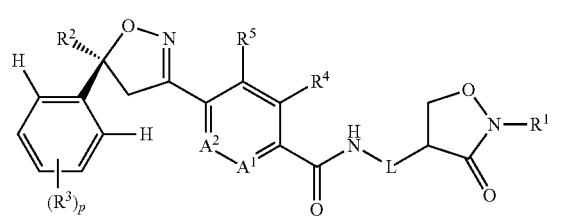

(I**)

Compounds of formula I** are more biologically active than compounds of formula I*. Component A may be a mixture of compounds I* and I in any ratio e.g. in a molar ratio of 1:99 to 99:1, e.g. 10:1 to 1:10, e.g. a substantially 50:50 molar ratio. Preferably component A is a racemic mixture of the compounds of formula I and I* or is enantiomerically enriched for the compound of formula I. For example, when component A is an enantiomerically enriched mixture of formula I, the molar proportion of compound I compared to the total amount of both enantiomers (in component A and therefore the mixture of the invention per se) is for example greater than 50%, e.g. at least 55, 60, 65, 70, 75, 80, 85, 90, 95, 96, 97, 98, or at least 99%. In one embodiment component A is a compound of formula I in substantially pure form, e.g. it is provided substantially in the absence of the alternative enantiomer.

Preferred compounds of formula I are shown in the Tables below.

TABLE A

Compounds of formula (I-a)

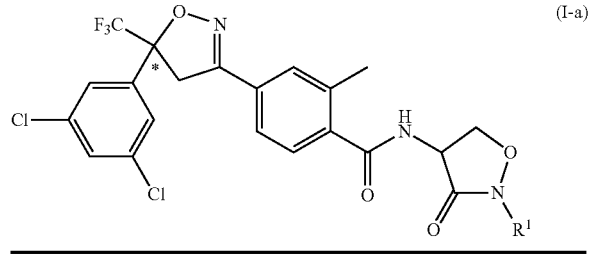

(I-a)

Table A provides 118 compounds and mixtures of formula (I-a) wherein $R^1$ has the values listed in table X below. The symbol * indicates the location of the chiral centre

TABLE B

Compounds of formula (Ib)

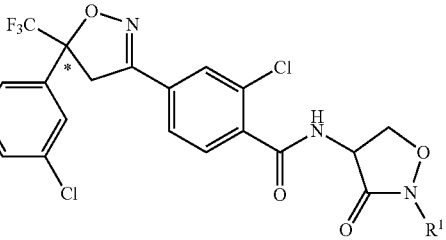

(I-b)

Table B provides 118 compounds and mixtures of formula (I-b) wherein $R^1$ has the values listed in table X below. The symbol * indicates the location of the chiral centre Table X represents Table A when X is A and Table B when X is B.

TABLE X

| Compound numbers | Stereochemistry at * | $R^1$ |
| --- | --- | --- |
| X.1 | Racemic mixture | ethyl- |
| X.2 | Racemic mixture | butyl- |
| X.3 | Racemic mixture | but-2-yl- |
| X.4 | Racemic mixture | 3-bromo-propyl- |
| X.5 | Racemic mixture | 2,2,2-trifluoro-ethyl- |
| X.6 | Racemic mixture | 3,3,3-trifluoro-propyl- |
| X.7 | Racemic mixture | 2-methoxy-ethyl- |
| X.8 | Racemic mixture | 1-methoxy-prop-2-yl- |
| X.9 | Racemic mixture | cyclobutyl- |
| X.10 | Racemic mixture | 2-methyl-cyclohex-1-yl- |
| X.11 | Racemic mixture | phenyl-methyl- |
| X.12 | Racemic mixture | 1-phenyl-eth-1-yl- |
| X.13 | Racemic mixture | 2-phenyl-eth-1-yl- |
| X.14 | Racemic mixture | (3-chloro-phenyl)-methyl- |
| X.15 | Racemic mixture | (2-fluoro-phenyl)-methyl- |
| X.16 | Racemic mixture | (4-methoxy-phenyl)-methyl- |
| X.17 | Racemic mixture | (2-trifluoromethyl-phenyl)-methyl- |
| X.18 | Racemic mixture | (2-trifluoromethoxy-phenyl)-methyl- |
| X.19 | Racemic mixture | (pyrid-2-yl)-methyl- |
| X.20 | Racemic mixture | (pyrid-3-yl)-methyl- |
| X.21 | Racemic mixture | (2-chloro-pyrid-5-yl)-methyl- |
| X.22 | Racemic mixture | (1-methyl-1H-imidazol-4-yl)-methyl- |
| X.23 | Racemic mixture | (furan-2-yl)-methyl- |
| X.24 | Racemic mixture | 2-(thiophen-2'-yl)-eth-1-yl- |
| X.25 | Racemic mixture | 2-(indol-3'-yl)-eth-1-yl- |
| X.26 | Racemic mixture | (1H-benzimidazol-2-yl)-methyl- |
| X.27 | Racemic mixture | (oxetan-2-yl)-methyl- |
| X.28 | Racemic mixture | (tetrahydrofuran-2-yl)-methyl- |
| X.29 | Racemic mixture | 2-([1',3']dioxolan-2'-yl)-eth-1-yl- |
| X.30 | Racemic mixture | 2-(morpholin-4'-yl)-eth-1-yl- |
| X.31 | Racemic mixture | 2-(benzo[1',3']dioxol-5'-yl)-eth-1-yl- |
| X.32 | Racemic mixture | (2,3-dihydro-benzo[1,4]dioxin-6-yl)-methyl- |
| X.33 | Racemic mixture | 2-chloro-phenyl- |
| X.34 | Racemic mixture | 3-fluoro-phenyl- |
| X.35 | Racemic mixture | 2-methyl-phenyl- |
| X.36 | Racemic mixture | 2-chloro-6-methyl-phenyl- |
| X.37 | Racemic mixture | 2-trifluoromethyl-phenyl- |
| X.38 | Racemic mixture | 2,4-dimethoxy-phenyl- |
| X.39 | Racemic mixture | 3-methyl-pyrid-2-yl- |
| X.40 | Racemic mixture | 1,3-dimethyl-1H-pyrazol-5-yl- |
| X.41 | Racemic mixture | 4-methyl-thiazol-2-yl- |
| X.42 | Racemic mixture | 5-methyl-thiadiazol-2-yl- |
| X.43 | Racemic mixture | quinolin-2-yl- |
| X.44 | Racemic mixture | quinolin-5-yl- |
| X.45 | Racemic mixture | benzothiazol-6-yl- |

TABLE X-continued

| Compound numbers | Stereochemistry at * | R¹ |
|---|---|---|
| X.46 | Racemic mixture | 4-methyl-benzothiazol-2-yl- |
| X.47 | Racemic mixture | thietan-3-yl- |
| X.48 | Racemic mixture | 1-oxo-thietan-3-yl- |
| X.49 | Racemic mixture | 1,1-dioxo-thietan-3-yl- |
| X.50 | Racemic mixture | 3-methyl-thietan-3-yl- |
| X.51 | Racemic mixture | oxetan-3yl |
| X.52 | Racemic mixture | tetrahydropyran-4-yl |
| X.53 | Racemic mixture | hydrogen |
| X.54 | Racemic mixture | methyl |
| X.55 | Racemic mixture | propyl |
| X.56 | Racemic mixture | 2,2-difluoro-ethyl- |
| X.57 | Racemic mixture | 2-fluoro-ethyl- |
| X.58 | S | ethyl- |
| X.59 | S | butyl- |
| X.60 | S | but-2-yl- |
| X.61 | S | 3-bromo-propyl- |
| X.62 | S | 2,2,2-trifluoro-ethyl- |
| X.63 | S | 3,3,3-trifluoro-propyl- |
| X.64 | S | 2-methoxy-ethyl- |
| X.65 | S | 1-methoxy-prop-2-yl- |
| X.66 | S | cyclobutyl- |
| X.67 | S | 2-methyl-cyclohex-1-yl- |
| X.68 | S | phenyl-methyl- |
| X.69 | S | 1-phenyl-eth-1-yl- |
| X.70 | S | 2-phenyl-eth-1-yl- |
| X.71 | S | (3-chloro-phenyl)-methyl- |
| X.72 | S | (2-fluoro-phenyl)-methyl- |
| X.73 | S | (4-methoxy-phenyl)-methyl- |
| X.74 | S | (2-trifluoromethyl-phenyl)-methyl- |
| X.75 | S | (2-trifluoromethoxy-phenyl)-methyl- |
| X.76 | S | (pyrid-2-yl)-methyl- |
| X.77 | S | (pyrid-3-yl)-methyl- |
| X.78 | S | (2-chloro-pyrid-5-yl)-methyl- |
| X.79 | S | (1-methyl-1H-imidazol-4-yl)-methyl- |
| X.80 | S | (furan-2-yl)-methyl- |
| X.81 | S | 2-(thiophen-2'-yl)-eth-1-yl- |
| X.82 | S | 2-(indol-3'-yl)-eth-1-yl- |
| X.83 | S | (1H-benzimidazol-2-yl)-methyl- |
| X.84 | S | (oxetan-2-yl)-methyl- |
| X.85 | S | (tetrahydrofuran-2-yl)-methyl- |
| X.86 | S | 2-([1',3']dioxolan-2'-yl)-eth-1-yl- |
| X.87 | S | 2-(morpholin-4'-yl)-eth-1-yl- |
| X.88 | S | 2-(benzo[1',3']dioxol-5'-yl)-eth-1-yl- |
| X.89 | S | (2,3-dihydro-benzo[1,4]dioxin-6-yl)-methyl- |
| X.90 | S | 2-chloro-phenyl- |
| X.91 | S | 3-fluoro-phenyl- |
| X.92 | S | 2-methyl-phenyl- |
| X.93 | S | 2-chloro-6-methyl-phenyl- |
| X.94 | S | 2-trifluoromethyl-phenyl- |
| X.95 | S | 2,4-dimethoxy-phenyl- |
| X.96 | S | 3-methyl-pyrid-2-yl- |
| X.97 | S | 1,3-dimethyl-1H-pyrazol-5-yl- |
| X.98 | S | 4-methyl-thiazol-2-yl- |
| X.99 | S | 5-methyl-thiadiazol-2-yl- |
| X.100 | S | quinolin-2-yl- |
| X.101 | S | quinolin-5-yl- |
| X.102 | S | benzothiazol-6-yl- |
| X.103 | S | 4-methyl-benzothiazol-2-yl- |
| X.104 | S | thietan-3-yl- |
| X.105 | S | 1-oxo-thietan-3-yl- |
| X.106 | S | 1,1-dioxo-thietan-3-yl- |
| X.107 | S | 3-methyl-thietan-3-yl- |
| X.108 | S | oxetan-3yl |
| X.109 | S | tetrahydropyran-4-yl |
| X.110 | S | hydrogen |
| X.111 | S | methyl |
| X.112 | S | propyl |
| X.113 | S | 2,2-difluoro-ethyl- |
| X.114 | S | 2-fluoro-ethyl- |
| X.115 | Racemic mixture | isopropyl |
| X.116 | Racemic mixture | cyclopropyl |
| X.117 | S | isopropyl |
| X.118 | S | cyclopropyl |

The present invention includes all isomers of compounds of formula (I), salts and N-oxides thereof, including enantiomers, diastereomers and tautomers. Component A may be a mixture of any type of isomer of a compound of formula I, or may be substantially a single type of isomer.

The compounds of the invention may be made by a variety of methods as shown in Schemes 1 to 3.

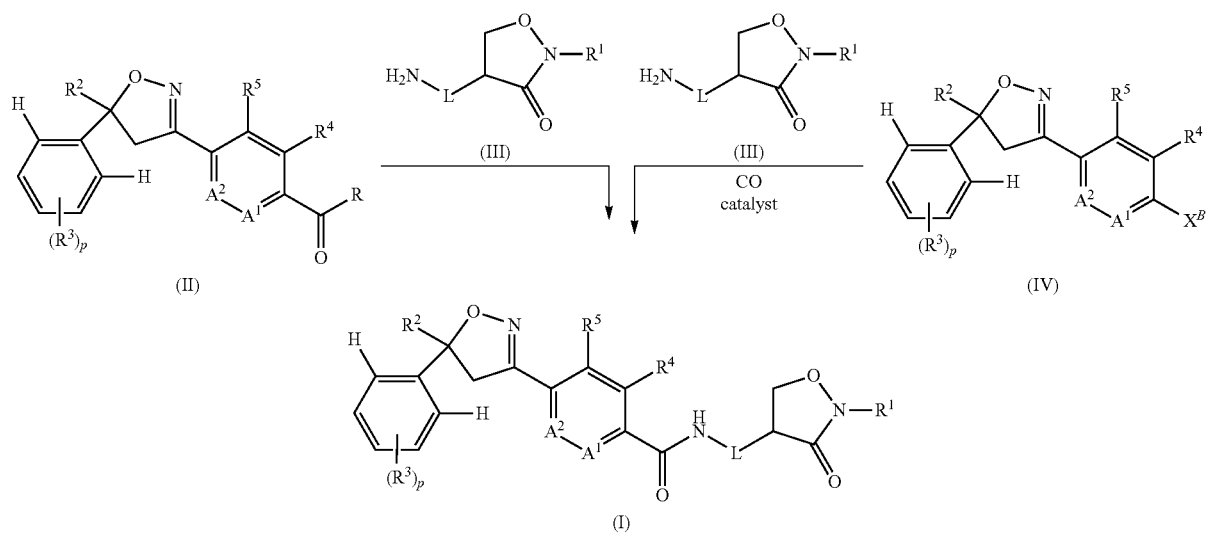

Scheme 1

1) Compounds of formula (I), can be prepared by reacting a compound of formula (II) wherein R is OH, $C_1$-$C_6$alkoxy or Cl, F or Br, with an amine of formula (III) as shown in Scheme 1. When R is OH such reactions are usually carried out in the presence of a coupling reagent, such as N,N'-dicyclohexyl-carbodiimide ("DCC"), 1-ethyl-3-(3-dimethylamino-propyl)carbodiimide hydrochloride ("EDC") or bis(2-oxo-3-oxazolidinyl)phosphonic chloride ("BOP-Cl"), in the presence of a base, and optionally in the presence of a nucleophilic catalyst, such as hydroxybenzotriazole ("HOBT"). When R is Cl, such reactions are usually carried out in the presence of a base, and optionally in the presence of a nucleophilic catalyst. Alternatively, it is possible to conduct the reaction in a biphasic system comprising an organic solvent, preferably ethyl acetate, and an aqueous solvent, preferably a solution of sodium hydrogen carbonate. When R is $C_1$-$C_6$alkoxy it is sometimes possible to convert the ester directly to the amide by heating the ester and amine together in a thermal process. Suitable bases include pyridine, triethylamine, 4-(dimethylamino)-pyridine ("DMAP") or diisopropylethylamine (Hunig's base). Preferred solvents are N,N-dimethylacetamide, tetrahydrofuran, dioxane, 1,2-dimethoxyethane, ethyl acetate and toluene. The reaction is carried out at a temperature of from 0° C. to 100° C., preferably from 15° C. to 30° C., in particular at ambient temperature. Amines of formula (III) are either known in the literature or can be prepared using methods known to a person skilled in the art.

2) Acid halides of formula (II), wherein R is Cl, F or Br, may be made from carboxylic acids of formula (II), wherein R is OH, under standard conditions, as described for example in WO09080250.

3) Carboxylic acids of formula (II), wherein R is OH, may be formed from esters of formula (II), wherein R is $C_1$-$C_6$alkoxy as described for example in WO09080250.

4) Compounds of formula (I) can be prepared by reacting a compound of formula (IV) wherein $X^B$ is a leaving group, for example a halogen, such as bromo, with carbon monoxide and an amine of formula (III), in the presence of a catalyst, such as palladium(II) acetate or bis(triphenylphosphine)palladium(II) dichloride, optionally in the presence of a ligand, such as triphenylphosphine, and a base, such as sodium carbonate, pyridine, triethylamine, 4-(dimethylamino)-pyridine ("DMAP") or diisopropylethylamine (Hunig's base), in a solvent, such as water, N,N-dimethylformamide or tetrahydrofuran. The reaction is carried out at a temperature of from 50° C. to 200° C., preferably from 100° C. to 150° C. The reaction is carried out at a pressure of from 50 to 200 bar, preferably from 100 to 150 bar.

5) Compounds of formula (IV) wherein $X^B$ is a leaving group, for example a halogen, such as bromo, can be made by a various of methods, for example as described in WO09080250.

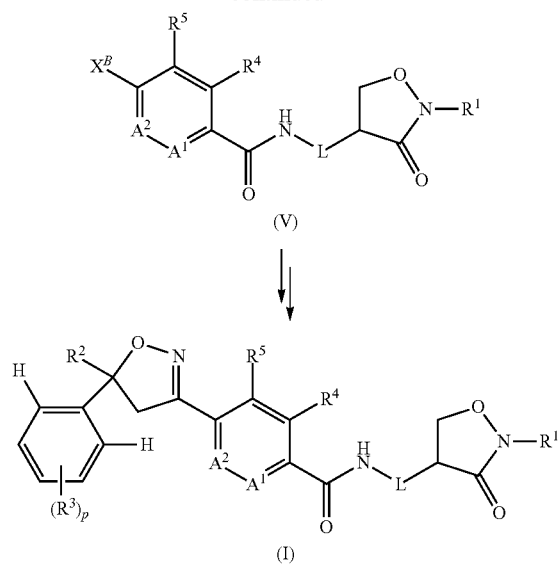

6) Alternatively, compounds of formula (I), can be prepared by various methods from an intermediate of formula (V) as shown in Scheme 2 wherein $X^B$ is a leaving group, for example a halogen, such as bromo, or $X^B$ is cyano, formyl or acetyl according to similar methods to those described in WO09080250. An intermediate of formula (V) can be prepared for example from an intermediate of formula (VI) as described in the same reference.

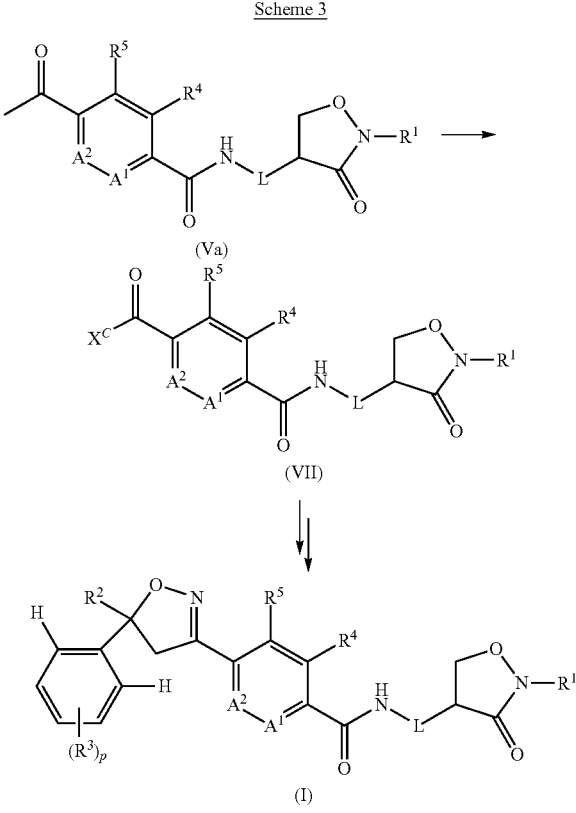

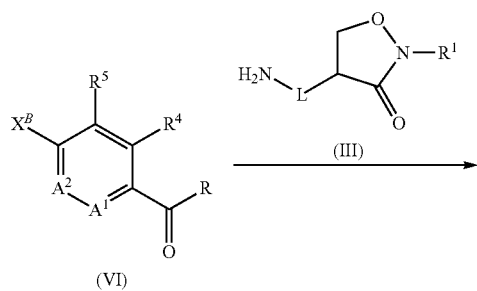

7) Alternatively, compounds of formula (I) can be prepared by various methods from an intermediate of formula (VII) as shown in Scheme 3 wherein $X^C$ is $X^C$-1 or $X^C$-2

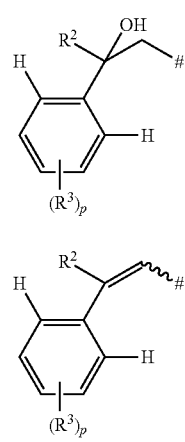

according to similar methods to those described in WO09080250.

8) Compounds of formula (VII) wherein $X^C$ is $X^C$ is $X^C$-1 or $X^C$-2 can be prepared from a compound of formula (Va) from a compound of formula (VII) wherein $X^C$ is $CH_2$-halogen using similar methods to those described in WO09080250.

9) Compounds of formula (VII) wherein $X^C$ is $CH_2$-halogen, such as bromo or chloro, can be prepared by reacting a methyl ketone of formula (Va) with a halogenating agent, such as bromine or chlorine, in a solvent, such as acetic acid, at a temperature of from 0° C. to 50° C., preferably from ambient temperature to 40° C.

Preferably, the combination product is for use against parasitic invertebrate pests, more preferably for use against parasitic invertebrate pests in or on an animal. Examples of pests include nematodes, trematodes, cestodes, flies, mites, tricks, lice, fleas, true bugs and maggots. The animal may be a non-human animal, e.g. an animal associated with agriculture, e.g. a cow, a pig, a sheep, a goat, a horse, or a donkey, or a companion animal, e.g. a dog or a cat.

In a further aspect the invention relates to a method of controlling parasitic invertebrate pests in or on an animal comprising administering an effective amount of the combination product. The administration may be for example oral administration, parenteral administration or external administration, e.g. to the surface of the animal body.

In a further aspect, the invention relates to a method of controlling parasitic invertebrate pests comprising administering an effective amount of the combination product to the environment in which an animal resides.

In a further aspect the invention provides a method of protecting an animal from a parasitic invertebrate pest comprising administering to the animal a pesticidally effective amount of the combination product of the invention. In a further aspect the invention provides the combination product for use in protecting an animal from a parasitic invertebrate pest. In a further aspect the invention provides use of the combination producing the manufacture of a medicament for protecting an animal from a parasitic invertebrate pest.

In a further aspect the invention provides a method of treating an animal suffering from a parasitic invertebrate pest comprising administering to the animal a pesticidally effective amount of the combination product of the invention. In a further aspect the invention provides a combination product for use in treating an animal suffering from a parasitic invertebrate pest. In a further aspect the invention provides use of the combination product in the manufacture of a medicament for treating an animal suffering from a parasitic invertebrate pest.

In a further aspect, the invention provides a pharmaceutical composition comprising component A and component B and a pharmaceutically suitable excipient.

Component A may be used in combination with anthelmintic agents. Such anthelmintic agents include, compounds selected from the macrocyclic lactone class of compounds such as ivermectin, avermectin, abamectin, emamectin, eprinomectin, doramectin, selamectin, moxidectin, nemadectin and milbemycin derivatives as described in EP-357460, EP-444964 and EP-594291. Additional anthelmintic agents include semisynthetic and biosynthetic avermectin/milbemycin derivatives such as those described in US-5015630, WO-9415944 and WO-9522552. Additional anthelmintic agents include the benzimidazoles such as albendazole, cambendazole, fenbendazole, flubendazole, mebendazole, oxfendazole, oxibendazole, parbendazole, and other members of the class. Additional anthelmintic agents include imidazothiazoles and tetrahydropyrimidines such as tetramisole, levamisole, pyrantel pamoate, oxantel or morantel. Additional anthelmintic agents include flukicides, such as triclabendazole and clorsulon and the cestocides, such as praziquantel and epsiprantel.

Component A may be used in combination with derivatives and analogues of the paraherquamide/marcfortine class of anthelmintic agents, as well as the antiparasitic oxazolines such as those disclosed in U.S. Pat. Nos. 5,478,855, 4,639, 771 and DE-19520936.

Component A may be used in combination with derivatives and analogues of the general class of dioxomorpholine antiparasitic agents as described in WO-9615121 and also with anthelmintic active cyclic depsipeptides such as those described in WO-9611945, WO-9319053, WO-9325543, EP-626375, EP-382173, WO-9419334, EP-382173, and EP-503538.

Component A may be used in combination with other ectoparasiticides; for example, fipronil; pyrethroids; organophosphates; insect growth regulators such as lufenuron; ecdysone agonists such as tebufenozide and the like; neonicotinoids such as imidacloprid and the like.

Component A may be used in combination with terpene alkaloids, for example those described in International Patent Application Publication Numbers WO95/19363 or WO04/72086, particularly the compounds disclosed therein.

Other examples of such biologically active compounds that component A may be used in combination with include but are not restricted to the following:

Organophosphates: acephate, azamethiphos, azinphosethyl, azinphos-methyl, bromophos, bromophos-ethyl, cadusafos, chlorethoxyphos, chlorpyrifos, chlorfenvinphos, chlormephos, demeton, demeton-S-methyl, demeton-S-methyl sulphone, dialifos, diazinon, dichlorvos, dicrotophos, dimethoate, disulfoton, ethion, ethoprophos, etrimfos, famphur, fenamiphos, fenitrothion, fensulfothion, fenthion, flupyrazofos, fonofos, formothion, fosthiazate, heptenophos, isazophos, isothioate, isoxathion, malathion, methacriphos, methamidophos, methidathion, methyl-parathion, mevinphos, monocrotophos, naled, omethoate, oxydemetonmethyl, paraoxon, parathion, parathion-methyl, phenthoate, phosalone, phosfolan, phosphocarb, phosmet, phosphamidon, phorate, phoxim, pirimiphos, pirimiphos-methyl, profenofos, propaphos, proetamphos, prothiofos, pyraclofos, pyridapenthion, quinalphos, sulprophos, temephos, terbufos, tebupirimfos, tetrachlorvinphos, thimeton, triazophos, trichlorfon, vamidothion. Carbamates: alanycarb, aldicarb, 2-sec-butylphenyl methylcarbamate, benfuracarb, carbaryl, carbofuran, carbosulfan, cloethocarb, ethiofencarb, fenoxycarb, fenthiocarb, furathiocarb, HCN-801, isoprocarb, indoxacarb, methiocarb, methomyl, 5-methyl-m-cumenylbutyryl (methyl)carbamate, oxamyl, pirimicarb, propoxur, thiodicarb, thiofanox, triazamate, UC-51717.

Pyrethroids: acrinathin, allethrin, alphametrin, 5-benzyl-3-furylmethyl (E)-(1R)-cis-2,2-dimethyl-3-(2-oxothiolan-3-ylidenemethyl)cyclopropanecarboxylate, bifenthrin, beta-cyfluthrin, cyfluthrin, a-cypermethrin, beta-cypermethrin, bioallethrin, bioallethrin((S)-cyclopentylisomer), bioresmethrin, bifenthrin, NCI-85193, cyclprothrin, cyhalothrin, cythithrin, cyphenothrin, deltamethrin, empenthrin, esfenvalerate, ethofenprox, fenfluthrin, fenpropathrin, fenvalerate, flucythrinate, flumethrin, fluvalinate (D isomer), imiprothrin, cyhalothrin, ?-cyhalothrin, permethrin, phenothrin, prallethrin, pyrethrins (natural products), resmethrin, tetramethrin, transfluthrin, theta-cypermethrin, silafluofen, t-fluvalinate, tefluthrin, tralomethrin, Zeta-cypermethrin.

Arthropod growth regulators: a) chitin synthesis inhibitors: benzoylureas: chlorfluazuron, diflubenzuron, fluazuron, flucycloxuron, flufenoxuron, hexaflumuron, lufenuron, novaluron, teflubenzuron, triflumuron, buprofezin, diofenolan, hexythiazox, etoxazole, chlorfentazine; b) ecdysone antagonists: halofenozide, methoxyfenozide, tebufenozide; c) juvenoids: pyriproxyfen, methoprene (including S-methoprene), fenoxycarb; d) lipid biosynthesis inhibitors: spirodiclofen.

Other antiparasitics: acequinocyl, amitraz, AKD-1022, ANS-118, azadirachtin, Bacillus thuringiensis, bensultap, bifenazate, binapacryl, bromopropylate, BTG-504, BTG-505, camphechlor, cartap, chlorobenzilate, chlordimeform, chlorfenapyr, chromafenozide, clothianidine, cyromazine, diacloden, diafenthiuron, DBI-3204, dinactin, dihydroxymethyldihydroxypyrrolidine, dinobuton, dinocap, endosulfan, ethiprole, ethofenprox, fenazaquin, flumite, MTI-800, fenpyroximate, fluacrypyrim, flubenzimine, flubrocythrinate, flufenzine, flufenprox, fluproxyfen, halofenprox, hydramethylnon, IKI-220, kanemite, NC-196, neem guard, nidinorterfuran, nitenpyram, SD-35651, WL-108477, pirydaryl, propargite, protrifenbute, pymethrozine, pyridaben, pyrimidifen, NC-1111, R-195, RH-0345, RH-2485, RYI-210, S-1283, S-1833, SI-8601, silafluofen, silomadine, spinosad, tebufenpyrad, tetradifon, tetranactin, thiacloprid, thiocyclam, thiamethoxam, tolfenpyrad, triazamate, triethoxyspinosyn, trinactin, verbutin, vertalec, YI-5301.

Fungicides: acibenzolar, aldimorph, ampropylfos, andoprim, azaconazole, azoxystrobin, benalaxyl, benomyl, bialaphos, blasticidin-S, Bordeaux mixture, bromuconazole, bupirimate, carpropamid, captafol, captan, carbendazim, chlorfenazole, chloroneb, chloropicrin, chlorothalonil, chlozolinate, copper oxychloride, copper salts, cyflufenamid, cymoxanil, cyproconazole, cyprodinil, cyprofuram, RH-7281, diclocymet, diclobutrazole, diclomezine, dicloran, difenoconazole, RP-407213, dimethomorph, domoxystrobin, diniconazole, diniconazole-M, dodine, edifenphos, epoxiconazole, famoxadone, fenamidone, fenarimol, fenbuconazole, fencaramid, fenpiclonil, fenpropidin, fenpropimorph, fentin acetate, fluazinam, fludioxonil, flumetover, flumorf/flumorlin, fentin hydroxide, fluoxastrobin, fluquinconazole, flusilazole, flutolanil, flutriafol, folpet, fosetyl-aluminium, furalaxyl, furametapyr, hexaconazole, ipconazole, iprobenfos, iprodione, isoprothiolane, kasugamycin, krsoxim-methyl, mancozeb, maneb, mefenoxam, mepronil, metalaxyl, metconazole, metominostrobin/fenominostrobin, metrafenone, myclobutanil, neo-asozin, nicobifen, orysastrobin, oxadixyl, penconazole, pencycuron, probenazole, prochloraz, propamocarb, propioconazole, proquinazid, prothioconazole, pyrifenox, pyraclostrobin, pyrimethanil, pyroquilon, quinoxyfen, spiroxamine, sulfur, tebuconazole, tetrconazole, thiabendazole, thifluzamide, thiophanate-methyl, thiram, tiadinil, triadimefon, triadimenol, tricyclazole, trifloxystrobin, triticonazole, validamycin, vinclozin.

Biological agents: Bacillus thuringiensis ssp aizawai, kurstaki, Bacillus thuringiensis delta endotoxin, baculovirus, entomopathogenic bacteria, virus and fungi.

Bactericides: chlortetracycline, oxytetracycline, streptomycin.

Other biological agents: enrofloxacin, febantel, penethamate, moloxicam, cefalexin, kanamycin, pimobendan, clenbuterol, omeprazole, tiamulin, benazepril, pyriprole, cefquinome, florfenicol, buserelin, cefovecin, tulathromycin, ceftiour, carprofen, metaflumizone, praziquarantel, triclabendazole.

Preferably, component B is imidacloprid, enrofloxacin, praziquantel, pyrantel embonate, febantel, penethamate, moloxicam, cefalexin, kanamycin, pimobendan, clenbuterol, fipronil, ivermectin, omeprazole, tiamulin, benazepril, milbemycin, cyromazine, thiamethoxam, pyriprole, deltamethrin, cefquinome, florfenicol, buserelin, cefovecin, tulathromycin, ceftiour, selamectin, carprofen, metaflumizone, moxidectin, methoprene (including S-methoprene), clorsulon, pyrantel, amitraz, triclabendazole, avermectin, abamectin, emamectin, eprinomectin, doramectin, selamectin, nemadectin, albendazole, cambendazole, fenbendazole, flubendazole, mebendazole, oxfendazole, oxibendazole, parbendazole, tetramisole, levamisole, pyrantel pamoate, oxantel, morantel, triclabendazole, epsiprantel, fipronil, lufenuron, ecdysone or tebufenozide.

More preferably, component B is enrofloxacin, praziquantel, pyrantel embonate, febantel, penethamate, moloxicam, cefalexin, kanamycin, pimobendan, clenbuterol, omeprazole, tiamulin, benazepril, pyriprole, cefquinome, florfenicol, buserelin, cefovecin, tulathromycin, ceftiour, selamectin, carprofen, moxidectin, clorsulon, pyrantel, eprinomectin, doramectin, selamectin, nemadectin, albendazole, cambendazole, fenbendazole, flubendazole, mebendazole, oxfendazole, oxibendazole, parbendazole, tetramisole, levamisole, pyrantel pamoate, oxantel, morantel, triclabendazole, epsiprantel, lufenuron or ecdysone.

Even more preferably, component B is enrofloxacin, praziquantel, pyrantel embonate, febantel, penethamate, moloxicam, cefalexin, kanamycin, pimobendan, clenbuterol, omeprazole, tiamulin, benazepril, pyriprole, cefquinome, florfenicol, buserelin, cefovecin, tulathromycin, ceftiour, selamectin, carprofen, moxidectin, clorsulon or pyrantel.

The invention also includes the following combinations:

A compound selected from Table A and Table B+imidacloprid.

A compound selected from Table A and Table B+enrofloxacin.

A compound selected from Table A and Table B+praziquantel.

A compound selected from Table A and Table B+pyrantel embonate.

A compound selected from Table A and Table B+febantel.

A compound selected from Table A and Table B+penethamate.

A compound selected from Table A and Table B+moloxicam.

A compound selected from Table A and Table B+cefalexin.
A compound selected from Table A and Table B+kanamycin.
A compound selected from Table A and Table B+pimobendan.
A compound selected from Table A and Table B+clenbuterol.
A compound selected from Table A and Table B+fipronil.
A compound selected from Table A and Table B+ivermectin.
A compound selected from Table A and Table B+omeprazole.
A compound selected from Table A and Table B+tiamulin.
A compound selected from Table A and Table B+benazepril.
A compound selected from Table A and Table B+milbemycin.
A compound selected from Table A and Table B+cyromazine.
A compound selected from Table A and Table B+thiamethoxam.
A compound selected from Table A and Table B+pyriprole.
A compound selected from Table A and Table B+deltamethrin.
A compound selected from Table A and Table B+cefquinome.
A compound selected from Table A and Table B+florfenicol.
A compound selected from Table A and Table B+buserelin.
A compound selected from Table A and Table B+cefovecin.
A compound selected from Table A and Table B+tulathromycin.
A compound selected from Table A and Table B+ceftiour.
A compound selected from Table A and Table B+selamectin.
A compound selected from Table A and Table B+carprofen.
A compound selected from Table A and Table B+metaflumizone.
A compound selected from Table A and Table B+moxidectin.
A compound selected from Table A and Table B+methoprene (including S-methoprene).
A compound selected from Table A and Table B+clorsulon.
A compound selected from Table A and Table B+pyrantel.
A compound selected from Table A and Table B+amitraz.
A compound selected from Table A and Table B+triclabendazole.
A compound selected from Table A and Table B+avermectin.
A compound selected from Table A and Table B+abamectin.
A compound selected from Table A and Table B+emamectin.
A compound selected from Table A and Table B+eprinomectin.
A compound selected from Table A and Table B+doramectin.
A compound selected from Table A and Table B+selamectin.
A compound selected from Table A and Table B+nemadectin.
A compound selected from Table A and Table B+albendazole.
A compound selected from Table A and Table B+cambendazole.
A compound selected from Table A and Table B+fenbendazole.
A compound selected from Table A and Table B+flubendazole.
A compound selected from Table A and Table B+mebendazole.
A compound selected from Table A and Table B+oxfendazole.
A compound selected from Table A and Table B+oxibendazole.
A compound selected from Table A and Table B+parbendazole.
A compound selected from Table A and Table B+tetramisole.
A compound selected from Table A and Table B+levamisole.
A compound selected from Table A and Table B+pyrantel pamoate.
A compound selected from Table A and Table B+oxantel.
A compound selected from Table A and Table B+morantel.
A compound selected from Table A and Table B+triclabendazole.
A compound selected from Table A and Table B+epsiprantel.
A compound selected from Table A and Table B+fipronil.
A compound selected from Table A and Table B+lufenuron.
A compound selected from Table A and Table B+ecdysone.
A compound selected from Table A and Table B+tebufenozide.

Examples of ratios of component A to component B include 100:1 to 1:6000, 50:1 to 1:50, 20:1 to 1:20, even more especially from 10:1 to 1:10, 5:1 to 1:5, 2:1 to 1:2, 4:1 to 2:1, 1:1, or 5:1, or 5:2, or 5:3, or 5:4, or 4:1, or 4:2, or 4:3, or 3:1, or 3:2, or 2:1, or 1:5, or 2:5, or 3:5, or 4:5, or 1:4, or 2:4, or 3:4, or 1:3, or 2:3, or 1:2, or 1:600, or 1:300, or 1:150, or 1:35, or 2:35, or 4:35, or 1:75, or 2:75, or 4:75, or 1:6000, or 1:3000, or 1:1500, or 1:350, or 2:350, or 4:350, or 1:750, or 2:750, or 4:750. Those mixing ratios are understood to include, on the one hand, ratios by weight and also, on other hand, molar ratios.

One skilled in the art recognizes that because in the environment and under physiological conditions salts of chemical compounds are in equilibrium with their corresponding non salt forms, salts share the biological utility of the non salt forms. Thus a wide variety of salts of components A and B are useful for control of invertebrate pests and animal parasites. The salts of components A and B include acid-addition salts with inorganic or organic acids such as hydrobromic, hydrochloric, nitric, phosphoric, sulfuric, acetic, butyric, fumaric, lactic, maleic, malonic, oxalic, propionic, salicylic, tartaric, 4-toluenesulfonic or valeric acids. Components A and B also include N-oxides. Accordingly, the invention comprises component A including N-oxides and salts thereof and component B including N-oxides and salts thereof.

The combination product may also contain formulation auxiliaries and additives, known to those skilled in the art as formulation aids (some of which may be considered to also function as solid diluents, liquid diluents or surfactants). Such formulation auxiliaries and additives may control: pH (buffers), foaming during processing (antifoams such polyorganosiloxanes), sedimentation of active ingredients (suspending agents), viscosity (thixotropic thickeners), in-container microbial growth (antimicrobials), product freezing (antifreezes), color (dyes/pigment dispersions), wash-off (film formers or stickers), evaporation (evaporation retardants), and other formulation attributes. Film formers include, for example, polyvinyl acetates, polyvinyl acetate copolymers, polyvinylpyrrolidone-vinyl acetate copolymer, polyvinyl alcohols, polyvinyl alcohol copolymers and waxes. Examples of formulation auxiliaries and additives include those listed in McCutcheon's Volume 2: Functional Materials, annual International and North American editions published by McCutcheon's Division, The Manufacturing Confectioner Publishing Co.; and PCT Publication WO 03/024222.

Of particular note is a combination product where component B has a different site of action from the compound of formula I. In certain instances, a combination with at least one other parasitic invertebrate pest control active ingredient having a similar spectrum of control but a different site of action will be particularly advantageous for resistance management. Thus, the combination product of the invention may comprise a compound of formula I and biologically effective amount of at least one additional parasitic invertebrate pest control active ingredient having a similar spectrum of control but a different site of action.

The combination products can be applied without other adjuvants, but most often application will be of a formulation comprising one or more active ingredients with suitable carriers, diluents, and surfactants and possibly in combination with a food depending on the contemplated end use. One method of application involves spraying a water dispersion or refined oil solution of the combination products. Combinations with spray oils, spray oil concentrates, spreader stickers, adjuvants, other solvents, and synergists such as piperonyl butoxide often enhance compound efficacy. Such sprays can be applied from spray containers such as a can, a bottle or other container, either by means of a pump or by releasing it from a pressurized container, e.g., a pressurized aerosol spray can. Such spray compositions can take various forms, for example, sprays, mists, foams, fumes or fog. Such spray compositions thus can further comprise propellants, foaming agents, etc. as the case may be. Of note is a spray composition comprising a biologically effective amount of the combination product and a carrier. One embodiment of such a spray composition comprises a biologically effective amount of a the combination product and a propellant. Representative propellants include, but are not limited to, methane, ethane, propane, butane, isobutane, butene, pentane, isopentane, neopentane, pentene, hydrofluorocarbons, chlorofluorocarbons, dimethyl ether, and mixtures of the foregoing. Of note is a spray composition (and a method utilizing such a spray composition dispensed from a spray container) used to control at least one parasitic invertebrate pest selected from the group consisting of mosquitoes, black flies, stable flies, deer flies, horse flies, wasps, yellow jackets, hornets, ticks, spiders, ants, gnats, and the like, including individually or in combinations.

The controlling of animal parasites includes controlling external parasites that are parasitic to the surface of the body of the host animal (e.g., shoulders, armpits, abdomen, inner part of the thighs) and internal parasites that are parasitic to the inside of the body of the host animal (e.g., stomach, intestine, lung, veins, under the skin, lymphatic tissue). External parasitic or disease transmitting pests include, for example, chiggers, ticks, lice, mosquitoes, flies, mites and fleas. Internal parasites include heartworms, hookworms and helminths. The combination products are particularly suitable for combating external parasitic pests. The combination products are suitable for systemic and/or non-systemic control of infestation or infection by parasites on animals.

The combination products are suitable for combating parasitic invertebrate pests that infest animal subjects including those in the wild, livestock and agricultural working animals. Livestock is the term used to refer (singularly or plurally) to a domesticated animal intentionally reared in an agricultural setting to make produce such as food or fiber, or for its labor; examples of livestock include cattle, sheep, goats, horses, pigs, donkeys, camels, buffalo, rabbits, hens, turkeys, ducks and geese (e.g., raised for meat, milk, butter, eggs, fur, leather, feathers and/or wool). By combating parasites, fatalities and performance reduction (in terms of meat, milk, wool, skins, eggs, etc.) are reduced, so that applying the combination product allows more economic and simple husbandry of animals.

The combination products are especially suitable for combating parasitic invertebrate pests that infest companion animals and pets (e.g., dogs, cats, pet birds and aquarium fish), research and experimental animals (e.g., hamsters, guinea pigs, rats and mice), as well as animals raised for/in zoos, wild habitats and/or circuses.

In an embodiment of this invention, the animal is preferably a vertebrate, and more preferably a mammal, avian or fish. In a particular embodiment, the animal subject is a mammal (including great apes, such as humans). Other mammalian subjects include primates (e.g., monkeys), bovine (e.g., cattle or dairy cows), porcine (e.g., hogs or pigs), ovine (e.g., goats or sheep), equine (e.g., horses), canine (e.g., dogs), feline (e.g., house cats), camels, deer, donkeys, buffalos, antelopes, rabbits, and rodents (e.g., guinea pigs, squirrels, rats, mice, gerbils, and hamsters). Avians include Anatidae (swans, ducks and geese), Columbidae (e.g., doves and pigeons), Phasianidae (e.g., partridges, grouse and turkeys), Thesienidae (e.g., domestic chickens), Psittacines (e.g., parakeets, macaws, and parrots), game birds, and ratites (e.g., ostriches).

Birds treated or protected by the combination product can be associated with either commercial or noncommercial aviculture. These include Anatidae, such as swans, geese, and ducks, Columbidae, such as doves and domestic pigeons, Phasianidae, such as partridge, grouse and turkeys, Thesienidae, such as domestic chickens, and Psittacines, such as parakeets, macaws and parrots raised for the pet or collector market, among others.

For purposes of the present invention, the term "fish" shall be understood to include without limitation, the Teleosti grouping of fish, i.e., teleosts. Both the Salmoniformes order (which includes the Salmonidae family) and the Perciformes order (which includes the Centrarchidae family) are contained within the Teleosti grouping. Examples of potential fish recipients include the Salmonidae, Serranidae, Sparidae, Cichlidae, and Centrarchidae, among others.

Other animals are also contemplated to benefit from the inventive methods, including marsupials (such as kangaroos), reptiles (such as farmed turtles), and other economically important domestic animals for which the inventive methods are safe and effective in treating or preventing parasite infection or infestation.

Examples of parasitic invertebrate pests controlled by administering a pesticidally effective amount of the combination products to an animal to be protected include ectoparasites (arthropods, acarines, etc.) and endoparasites (helminths, e.g., nematodes, trematodes, cestodes, acanthocephalans, etc.).

The disease or group of diseases described generally as helminthiasis is due to infection of an animal host with parasitic worms known as helminths. The term 'helminths' is meant to include nematodes, trematodes, cestodes and acanthocephalans. Helminthiasis is a prevalent and serious economic problem with domesticated animals such as swine, sheep, horses, cattle, goats, dogs, cats and poultry.

Among the helminths, the group of worms described as nematodes causes widespread and at times serious infection in various species of animals. Nematodes that are contemplated to be treated by the combination products of the invention and by the inventive methods include, without limitation, the following genera: *Acanthocheilonema, Aelurostrongylus, Ancylostoma, Angiostrongylus, Ascaridia, Ascaris, Brugia, Bunostomum, Capillaria, Chabertia, Cooperia, Crenosoma, Dictyocaulus, Dioctophyme, Dipetalonema, Diphyllobothrium, Dirofilaria, Dracunculus, Enterobius, Filaroides, Haemonchus, Heterakis, Lagochilascaris, Loa, Mansonella, Muellerius, Necator, Nematodirus, Oesophagostomum, Ostertagia, Oxyuris, Parafilaria, Parascaris, Physaloptera, Protostrongylus, Setaria, Spirocerca, Stephanofilaria, Strongyloides, Strongylus, Thelazia, Toxascaris, Toxocara, Trichinella, Trichonema, Trichostrongylus, Trichuris, Uncinaria* and *Wuchereria*.

Of the above, the most common genera of nematodes infecting the animals referred to above are *Haemonchus, Trichostrongylus, Ostertagia, Nematodirus, Cooperia, Ascaris, Bunostomum, Oesophagostomum, Chabertia, Trichuris, Strongylus, Trichonema, Dictyocaulus, Capillaria,*

*Heterakis, Toxocara, Ascaridia, Oxyuris, Ancylostoma, Uncinaria, Toxascaris* and *Parascaris*. Certain of these, such as *Nematodirus, Cooperia* and *Oesophagostomum* attack primarily the intestinal tract while others, such as *Haemonchus* and *Ostertagia*, are more prevalent in the stomach while others such as *Dictyocaulus* are found in the lungs. Still other parasites may be located in other tissues such as the heart and blood vessels, subcutaneous and lymphatic tissue and the like.

Trematodes that are contemplated to be treated by the invention and by the inventive methods include, without limitation, the following genera: *Alaria, Fasciola, Nanophyetus, Opisthorchis, Paragonimus* and *Schistosoma*.

Cestodes that are contemplated to be treated by the invention and by the inventive methods include, without limitation, the following genera: *Diphyllobothrium, Diplydium, Spirometra* and *Taenia*.

The most common genera of parasites of the gastrointestinal tract of humans are *Ancylostoma, Necator, Ascaris, Strongy hides, Trichinella, Capillaria, Trichuris* and *Enterobius*. Other medically important genera of parasites which are found in the blood or other tissues and organs outside the gastrointestinal tract are the filarial worms such as *Wuchereria, Brugia, Onchocerca* and *Loa*, as well as *Dracunculus* and extra intestinal stages of the intestinal worms *Strongyloides* and *Trichinella*.

Numerous other helminth genera and species are known to the art, and are also contemplated to be treated by the combination products. These are enumerated in great detail in Textbook of Veterinary Clinical Parasitology, Volume 1, Helminths, E. J. L. Soulsby, F. A. Davis Co., Philadelphia, Pa.; Helminths, Arthropods and Protozoa, (6$^{th}$ Edition of Monnig's Veterinary Helminthology and Entomology), E. J. L. Soulsby, Williams and Wilkins Co., Baltimore, Md.

The combination products are effective against a number of animal ectoparasites (e.g., arthropod ectoparasites of mammals and birds).

Insect and acarine pests include, e.g., biting insects such as flies and mosquitoes, mites, ticks, lice, fleas, true bugs, parasitic maggots, and the like.

Adult flies include, e.g., the horn fly or *Haematobia irritans*, the horse fly or *Tabanus* spp., the stable fly or *Stomoxys calcitrans*, the black fly or *Simulium* spp., the deer fly or *Chrysops* spp., the louse fly or *Melophagus ovinus*, and the tsetse fly or *Glossina* spp. Parasitic fly maggots include, e.g., the bot fly (*Oestrus ovis* and *Cuterebra* spp.), the blow fly or *Phaenicia* spp., the screwworm or *Cochliomyia hominivorax*, the cattle grub or *Hypoderma* spp., the fleeceworm and the *Gastrophilus* of horses. Mosquitoes include, for example, *Culex* spp., *Anopheles* spp. and *Aedes* spp.

Mites include *Mesostigmalphatalpha* spp. e.g., mesostigmatids such as the chicken mite, *Dermalphanyssus galphallinalphae*; itch or scab mites such as *Sarcoptidae* spp. for example, *Salpharcoptes scalphabiei*; mange mites such as *Psoroptidae* spp. including *Chorioptes bovis* and *Psoroptes ovis*; chiggers e.g., *Trombiculidae* spp. for example the North American chigger, *Trombiculalpha alphalfreddugesi*.

Ticks include, e.g., soft-bodied ticks including *Argasidae* spp. for example *Argalphas* spp. and *Ornithodoros* spp.; hard-bodied ticks including *Ixodidae* spp., for example *Rhipicephalphalus sanguineus, Dermacentor variabilis, Dermacentor andersoni, Amblyomma americanum, Ixodes scapularis* and other *Rhipicephalus* spp. (including the former *Boophilus* genera).

Lice include, e.g., sucking lice, e.g., *Menopon* spp. and *Bovicola* spp.; biting lice, e.g., *Haematopinus* spp., *Linognathus* spp. and *Solenopotes* spp.

Fleas include, e.g., *Ctenocephalides* spp., such as dog flea (*Ctenocephalides canis*) and cat flea (*Ctenocephalides felis*); *Xenopsylla* spp. such as oriental rat flea (*Xenopsylla cheopis*); and *Pulex* spp. such as human flea (*Pulex irritans*).

True bugs include, e.g., *Cimicidae* or e.g., the common bed bug (*Cimex lectularius*); *Triatominae* spp. including triatomid bugs also known as kissing bugs; for example *Rhodnius prolixus* and *Triatoma* spp.

Generally, flies, fleas, lice, mosquitoes, gnats, mites, ticks and helminths cause tremendous losses to the livestock and companion animal sectors. Arthropod parasites also are a nuisance to humans and can vector disease-causing organisms in humans and animals. Numerous other parasitic invertebrate pests are known to the art, and are also contemplated to be treated by the combination products. These are enumerated in great detail in Medical and Veterinary Entomology, D. S. Kettle, John Wiley AND Sons, New York and Toronto; Control of Arthropod Pests of Livestock: A Review of Technology, R. O. Drummand, J. E. George, and S. E. Kunz, CRC Press, Boca Raton, Fla.

The combination products may also be effective against ectoparasites including: flies such as *Haematobia* (*Lyperosia*) *irritans* (horn fly), *Simulium* spp. (blackfly), *Glossina* spp. (tsetse flies), *Hydrotaea irritans* (head fly), *Musca autumnalis* (face fly), *Musca domestica* (house fly), *Morellia simplex* (sweat fly), *Tabanus* spp. (horse fly), *Hypoderma bovis, Hypoderma lineatum, Lucilia sericata, Lucilia cuprina* (green blowfly), *Calliphora* spp. (blowfly), *Protophormia* spp., *Oestrus ovis* (nasal botfly), *Culicoides* spp. (midges), *Hippobosca equine, Gastrophilus intestinalis, Gastrophilus haemorrhoidalis* and *Gastrophilus nasalis*; lice such as *Bovicola* (Damalinia) *bovis, Bovicola equi, Haematopinus asini, Felicola subrostratus, Heterodoxus spiniger, Lignonathus setosus* and *Trichodectes canis*; keds such as *Melophagus ovinus*; and mites such as *Psoroptes* spp., *Sarcoptes scabei, Chorioptes bovis, Demodex equi, Cheyletiella* spp., *Notoedres cati, Trombicula* spp. and *Otodectes cyanotis* (ear mites).

Treatments of the invention are by conventional means such as by enteral administration in the form of, for example, tablets, capsules, drinks, drenching preparations, granulates, pastes, boli, feed-through procedures, or suppositories; or by parenteral administration, such as, for example, by injection (including intramuscular, subcutaneous, intravenous, intraperitoneal) or implants; or by nasal administration.

The components A and B may be administered separately e.g. as separate compositions. In this case, the components may be administered simultaneously or sequentially. Alternatively, the components A and B may be components of one composition.

The combination products may be administered in a controlled release form, for example in subcutaneous or orally adminstered slow release formulations.

Typically a parasiticidal composition according to the present invention comprises components A and B, or N-oxides or salts thereof, with one or more pharmaceutically or veterinarily acceptable carriers comprising excipients and auxiliaries selected with regard to the intended route of administration (e.g., oral or parenteral administration such as injection) and in accordance with standard practice. In addition, a suitable carrier is selected on the basis of compatibility with the one or more active ingredients in the composition, including such considerations as stability relative to pH and moisture content. Therefore of note is a composition for protecting an animal from an invertebrate parasitic pest comprising a parasitically effective amount of the combination product and at least one carrier.

For parenteral administration including intravenous, intramuscular and subcutaneous injection, the combination product can be formulated in suspension, solution or emulsion in oily or aqueous vehicles, and may contain adjuncts such as suspending, stabilizing and/or dispersing agents.

The combination product may also be formulated for bolus injection or continuous infusion. Pharmaceutical compositions for injection include aqueous solutions of water-soluble forms of active ingredients (e.g., a salt of an active compound), preferably in physiologically compatible buffers containing other excipients or auxiliaries as are known in the art of pharmaceutical formulation. Additionally, suspensions of the active compounds may be prepared in a lipophilic vehicle. Suitable lipophilic vehicles include fatty oils such as sesame oil, synthetic fatty acid esters such as ethyl oleate and triglycerides, or materials such as liposomes.

Aqueous injection suspensions may contain substances that increase the viscosity of the suspension, such as sodium carboxymethyl cellulose, sorbitol, or dextran. Formulations for injection may be presented in unit dosage form, e.g., in ampoules or in multi-dose containers. Alternatively, the active ingredient may be in powder form for constitution with a suitable vehicle, e.g., sterile, pyrogen-free water, before use.

In addition to the formulations described supra, the combination products may also be formulated as a depot preparation. Such long acting formulations may be administered by implantation (for example, subcutaneously or intramuscularly) or by intramuscular or subcutaneous injection.

The combination products may be formulated for this route of administration with suitable polymeric or hydrophobic materials (for instance, in an emulsion with a pharmacologically acceptable oil), with ion exchange resins, or as a sparingly soluble derivative such as, without limitation, a sparingly soluble salt.

For administration by inhalation, the combination products can be delivered in the form of an aerosol spray using a pressurized pack or a nebulizer and a suitable propellant, e.g., without limitation, dichlorodifluoromethane, trichlorofluoromethane, dichlorotetrafluoroethane or carbon dioxide. In the case of a pressurized aerosol, the dosage unit may be controlled by providing a valve to deliver a metered amount. Capsules and cartridges of, for example, gelatin for use in an inhaler or insufflator may be formulated containing a powder mix of the compound and a suitable powder base such as lactose or starch.

The combination products may have favorable pharmacokinetic and pharmacodynamic properties providing systemic availability from oral administration and ingestion. Therefore after ingestion by the animal to be protected, parasiticidally effective concentrations of the combination products in the bloodstream may protect the treated animal from blood-sucking pests such as fleas, ticks and lice. Therefore of note is a composition for protecting an animal from an invertebrate parasite pest in a form for oral administration (i.e. comprising, in addition to a parasiticidally effective amount of a the combination products, one or more carriers selected from binders and fillers suitable for oral administration and feed concentrate carriers).

For oral administration in the form of solutions (the most readily available form for absorption), emulsions, suspensions, pastes, gels, capsules, tablets, boluses, powders, granules, rumen-retention and feed/water/lick blocks, the combination products can be formulated with binders/fillers known in the art to be suitable for oral administration compositions, such as sugars and sugar derivatives (e.g., lactose, sucrose, mannitol, sorbitol), starch (e.g., maize starch, wheat starch, rice starch, potato starch), cellulose and derivatives (e.g., methylcellulose, carboxymethylcellulose, ethylhydroxycellulose), protein derivatives (e.g., zein, gelatin), and synthetic polymers (e.g., polyvinyl alcohol, polyvinylpyrrolidone). If desired, lubricants (e.g., magnesium stearate), disintegrating agents (e.g., cross-linked polyvinylpyrrolidinone, agar, alginic acid) and dyes or pigments can be added. Pastes and gels often also contain adhesives (e.g., acacia, alginic acid, bentonite, cellulose, xanthan gum, colloidal magnesium aluminum silicate) to aid in keeping the composition in contact with the oral cavity and not being easily ejected.

A preferred embodiment is a composition of the present method formulated into a chewable and/or edible product (e.g., a chewable treat or edible tablet). Such a product would ideally have a taste, texture and/or aroma favored by the animal to be protected so as to facilitate oral administration of the combination products.

If the parasiticidal compositions are in the form of feed concentrates, the carrier is typically selected from high-performance feed, feed cereals or protein concentrates. Such feed concentrate-containing compositions can, in addition to the parasiticidal active ingredients, comprise additives promoting animal health or growth, improving quality of meat from animals for slaughter or otherwise useful to animal husbandry.

These additives can include, for example, vitamins, antibiotics, chemotherapeutics, bacteriostats, fungistats, coccidiostats and hormones.

The combination product may also be formulated in rectal compositions such as suppositories or retention enemas, using, e.g., conventional suppository bases such as cocoa butter or other glycerides.

The formulations for the method of this invention may include an antioxidant, such asBHT (butylated hydroxytoluene). The antioxidant is generally present in amounts of at 0.1-5 percent (wt/vol). Some of the formulations require a solubilizer, such as oleic acid, to dissolve the active agent, particularly if spinosad is included. Common spreading agents used in these pour-on formulations include isopropyl myristate, isopropyl palmitate, caprylic/capric acid esters of saturated $C_{12}$-$C_{18}$ fatty alcohols, oleic acid, oleyl ester, ethyl oleate, triglycerides, silicone oils and dipropylene glycol methyl ether. The pour-on formulations for the method of this invention are prepared according to known techniques. Where the pour-on is a solution, the parasiticide/insecticide is mixed with the carrier or vehicle, using heat and stirring if required. Auxiliary or additional ingredients can be added to the mixture of active agent and carrier, or they can be mixed with the active agent prior to the addition of the carrier. Pour-on formulations in the form of emulsions or suspensions are similarly prepared using known techniques.

Other delivery systems for relatively hydrophobic pharmaceutical compounds may be employed. Liposomes and emulsions are well-known examples of delivery vehicles or carriers for hydrophobic drugs. In addition, organic solvents such as dimethylsulfoxide may be used, if needed.

The rate of application required for effective parasitic invertebrate pest control (i.e. "pesticidally effective amount") will depend on such factors as the species of parasitic invertebrate pest to be controlled, the pest's life cycle, life stage, its size, location, time of year, host crop or animal, feeding behavior, mating behavior, ambient moisture, temperature, and the like. One skilled in the art can easily determine the pesticidally effective amount necessary for the desired level of parasitic invertebrate pest control.

In general for veterinary use, the combination products are administered in a pesticidally effective amount to an animal, particularly a homeothermic animal, to be protected from parasitic invertebrate pests.

A pesticidally effective amount is the amount of active ingredient needed to achieve an observable effect diminishing the occurrence or activity of the target parasitic invertebrate pest. One skilled in the art will appreciate that the pesticidally effective dose can vary for the various compounds and compositions useful for the method of the present invention, the desired pesticidal effect and duration, the target parasitic invertebrate pest species, the animal to be protected, the mode of application and the like, and the amount needed to achieve a particular result can be determined through simple experimentation.

For oral or parenteral administration to animals, a dose of the combination product of the present invention administered at suitable intervals typically ranges from about 0.01 mg/kg to about 100 mg/kg, and preferably from about 0.01 mg/kg to about 30 mg/kg of animal body weight.

Suitable intervals for the administration of the combination products of the present invention to animals range from about daily to about yearly. Of note are administration intervals ranging from about weekly to about once every 6 months. Of particular note are monthly administration intervals (i.e. administering the compounds to the animal once every month).

The invention claimed is:

1. A method of administering a combination product comprising a component A and a component B, wherein component A is a compound of formula (I)

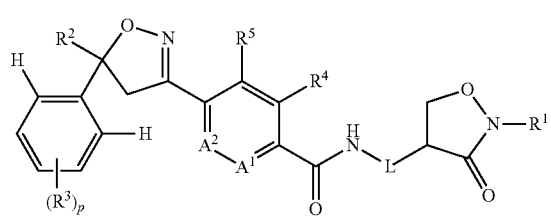

(I)

wherein
L is a direct bond or methylene;
$A^1$ and $A^2$ are C—H, or one of $A^1$ and $A^2$ is C—H and the other is N;
$R^1$ is hydrogen, cyano, cyano-$C_1$-$C_8$alkyl, $C_1$-$C_8$alkyl, $C_1$-$C_8$haloalkyl, $C_3$-$C_8$cycloalkyl, $C_3$-$C_8$cycloalkyl where one carbon atom is replaced by O, S, S(O) or $SO_2$, or $C_3$-$C_8$cycloalkyl-$C_1$-$C_8$alkyl, $C_3$-$C_8$cycloalkyl-$C_1$-$C_8$alkyl where one carbon atom in the cycloalkyl group is replaced by O, S, S(O) or $SO_2$, or $C_3$-$C_8$cycloalkyl-$C_1$-$C_8$haloalkyl, $C_1$-$C_8$hydroxyalkyl, $C_1$-$C_8$alkoxy-$C_1$-$C_8$alkyl, $C_2$-$C_8$alkenyl, $C_2$-$C_8$haloalkenyl, $C_2$-$C_8$alkynyl, $C_2$-$C_8$haloalkynyl, phenyl, phenyl substituted by one to three $R^6$, phenyl-$C_1$-$C_4$alkyl, phenyl-$C_1$-$C_4$alkyl wherein the phenyl moiety is substituted by one to three $R^6$, 5-6 membered heteroaryl-$C_1$-$C_4$alkyl or 5-6 membered heteroaryl-$C_1$-$C_4$alkyl wherein the heteroaryl moiety is substituted by one to three $R^6$, or $C_1$-$C_4$alkyl-($C_1$-$C_4$alkyl-O—N=)C—$CH_2$—;
$R^2$ is chlorodifluoromethyl or trifluoromethyl;
each $R^3$ is independently bromo, chloro, fluoro or trifluoromethyl;
$R^4$ is hydrogen, halogen, methyl, halomethyl or cyano;
$R^5$ is hydrogen;
or $R^4$ and $R^5$ together form a bridging 1,3-butadiene group;
each $R^6$ is independently halogen, cyano, nitro, $C_1$-$C_8$alkyl, $C_1$-$C_8$haloalkyl, $C_1$-$C_8$alkoxy, or $C_1$-$C_8$haloalkoxy;
p is 2 or 3;
and component B is a further therapeutic agent selected from the group consisting of imidacloprid, enrofloxacin, praziquantel, pyrantel embonate, febantel, penethamate, moloxicam, cefalexin, kanamycin, pimobendan, clenbuterol, fipronil, ivermectin, omeprazole, tiamulin, benazepril, milbemycin, cyromazine, thiamethoxam, pyriprole, deltamethrin, cefquinome, florfenicol, buserelin, cefovecin, tulathromycin, ceftiour, selamectin, carprofen, metaflumizone, moxidectin, methoprene, S-methoprene, clorsulon, pyrantel, amitraz, triclabendazole, avermectin, abamectin, emamectin, eprinomectin, doramectin, nemadectin, albendazole, cambendazole, fenbendazole, flubendazole, mebendazole, oxfendazole, oxibendazole, parbendazole, tetramisole, levamisole, pyrantel pamoate, oxantel, morantel, epsiprantel, lufenuron, ecdysone, tebufenozide, lufenuron, ecdysone, and enrofloxacin;
wherein the combination product is administered to an animal.

2. The method according to claim 1, wherein $A^1$ and $A^2$ are C—H; $R^2$ is trifluoromethyl, and $R^5$ is hydrogen.

3. The method according to claim 1, wherein $A^1$ and $A^2$ are C—H; $R^2$ is trifluoromethyl, $R^4$ is methyl, $R^5$ is hydrogen, each $R^3$ is chlorine, p is 2.

4. The method according to claim 1, wherein $R^1$ is independently hydrogen, methyl, ethyl, propyl, butyl, cyclopropyl, cyclopropyl-methyl, cyclobutyl, cyclobutyl-methyl, oxetanyl, thietanyl, trifluoroethyl, difluoroethyl, allyl, propargyl, cyanomethyl, cyanoethyl, benzyl, benzyl substituted by one to three $R^6$, or $R^1$ is pyridyl-methyl-or pyridyl-methyl- substituted by one to three $R^6$, and each $R^6$ is independently fluoro, chloro, bromo, trifluoromethyl, trifluoromethoxy, cyano or methoxy.

5. The method according to claim 1, wherein component A is a mixture of compounds I* and I**

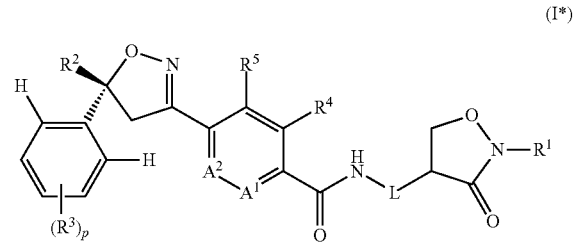

(I*)

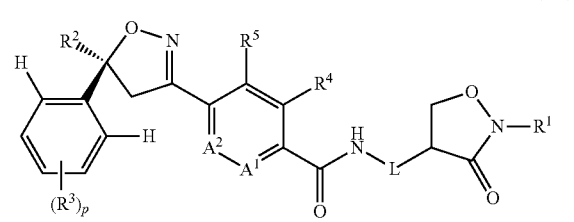

(I**)

wherein the molar proportion of compound I** compared to the total amount of both enantiomers is greater than 50%.

6. The method according to claim 1, wherein the combination product is for use against parasitic invertebrate pests.

7. The method according to claim 1, wherein the combination product is for use against parasitic invertebrate pests in or on an animal.

8. The method according to claim 7, wherein the pest is a nematode, a trematode, a cestode, a fly, a mite, a tick, a lice, a flea, a true bug or a maggot.

9. The method according to claim 7, wherein the animal to be treated is a cow, a pig, a sheep, a goat, a dog, a cat, a horse, and/or a donkey.

10. A method according to claim 1, wherein said administration is oral administration, parenteral administration or external administration.

11. The method of claim 1 further comprising a method of controlling parasitic invertebrate pests by applying the combination product to the environment in which an animal resides.

* * * * *